United States Patent
Shipp et al.

(10) Patent No.: US 7,608,080 B2
(45) Date of Patent: Oct. 27, 2009

(54) DEVICE FOR INSERTING IMPLANTS

(75) Inventors: Kenneth Shipp, Colliersville, TN (US); Dusty Anna Parker Needham, Eads, TN (US); Benjamin Garden, North Webster, IN (US); Roger Ousley, Southaven, MS (US)

(73) Assignee: Warsaw Orthopedic, Inc.

( * ) Notice: Subject to any disclaimer, the term of this patent is extended or adjusted under 35 U.S.C. 154(b) by 964 days.

(21) Appl. No.: 10/884,362

(22) Filed: Jul. 2, 2004

(65) Prior Publication Data

US 2006/0004376 A1    Jan. 5, 2006

(51) Int. Cl.
*A61B 17/58* (2006.01)
(52) U.S. Cl. ........................................................ 606/99
(58) Field of Classification Search .................. 606/90, 606/99, 110–115, 205–208, 127, 128; 623/16.11, 623/17.11–17.16
See application file for complete search history.

(56) References Cited

U.S. PATENT DOCUMENTS

| | | | | |
|---|---|---|---|---|
| 3,955,578 | A * | 5/1976 | Chamness et al. | 606/47 |
| 4,375,174 | A * | 3/1983 | Shanley, Jr. | 81/165 |
| 4,454,791 | A * | 6/1984 | Seward, III | 81/133 |
| 5,167,662 | A | 12/1992 | Hayes et al. | |
| 5,258,007 | A * | 11/1993 | Spetzler et al. | 606/208 |
| 5,599,279 | A * | 2/1997 | Slotman et al. | 600/201 |
| 5,644,957 | A * | 7/1997 | Gustafson et al. | 81/165 |
| 5,720,751 | A * | 2/1998 | Jackson | 606/86 |
| 5,732,992 | A | 3/1998 | Mauldin | |
| 5,782,830 | A | 7/1998 | Farris | |
| 6,066,174 | A | 5/2000 | Farris | |
| 6,174,311 | B1 | 1/2001 | Branch et al. | |
| 6,319,257 | B1 * | 11/2001 | Carignan et al. | 606/99 |
| 6,569,168 | B2 | 5/2003 | Lin | |
| 6,610,065 | B1 | 8/2003 | Branch et al. | |
| 6,652,533 | B2 | 11/2003 | O'Neil | |
| 6,663,638 | B2 | 12/2003 | Ralph et al. | |
| 6,666,866 | B2 | 12/2003 | Martz et al. | |
| 6,712,819 | B2 | 3/2004 | Zucherman et al. | |
| 7,169,182 | B2 * | 1/2007 | Errico et al. | 623/17.15 |
| 2002/0058950 | A1 | 5/2002 | Winterbottom et al. | |
| 2002/0072752 | A1 | 6/2002 | Zucherman et al. | |
| 2002/0161375 | A1 | 10/2002 | Ralph et al. | |
| 2002/0188295 | A1 | 12/2002 | Martz et al. | |
| 2003/0083747 | A1 | 5/2003 | Winterbottom et al. | |
| 2003/0130667 | A1 | 7/2003 | Lin | |
| 2003/0149438 | A1 | 8/2003 | Nichols | |
| 2003/0229355 | A1 | 12/2003 | Keller | |

* cited by examiner

*Primary Examiner*—Eduardo C Robert
*Assistant Examiner*—Tara R George (57) ABSTRACT

A device for inserting implants comprises an elongate, hollow shank with a gripping head at one end to grip and hold an implant. The gripping head includes a movable jaw operatively connected to a drive shaft such that rotation of the drive shaft causes the movable jaw to move. The drive shaft may include a gear that meshes with integrally formed teeth on the movable jaw. The drive shaft is axially movable between locked and unlocked positions.

32 Claims, 9 Drawing Sheets

DEVICE FOR INSERTING IMPLANTS

BACKGROUND

The present invention relates generally to surgical instruments and more particularly to implant holders and inserters for inserting implants into the body.

The spinal disk resides between adjacent vertebral bodies and allows for relative motion between the vertebrae in a healthy spine. With disease and/or degeneration, a spinal disk may become painful and/or mechanically insufficient warranting surgical fusion across the affected disk. Present methods of inserting a spinal implant or interbody spacer between adjacent vertebrae generally include the use of a holder and a secondary device for the delivery of the implant to the final location.

SUMMARY

The present invention provides a method and apparatus for inserting an implant, such as a spinal implant, into the body using a single instrument. The present invention comprises a surgical instrument having an elongate hollow shank with a gripping head at one end. The gripping head includes a movable jaw to grip and hold the implant during an insertion procedure. An actuating mechanism is operatively connected with the movable jaw. The actuating mechanism includes a drive shaft extending through the shank and rotatable about a longitudinal axis. The drive shaft may include a drive gear that meshes with a first set of teeth on the movable jaw. Rotation of the drive shaft causes the movable jaw to move. When the drive shaft is rotated in a first direction, the movable jaw closes on the implant. When the drive shaft is rotated in a second direction, the movable jaw opens to release the implant.

In another aspect of the invention, the drive shaft is axially movable between locked and unlocked positions. In the unlocked position, the drive shaft can be rotated to drive the movable jaw. In the locked position, the drive shaft is locked to prevent rotation.

In another aspect of the invention, the drive shaft comprises a flexible drive shaft. The flexible drive includes first and second end portions connected by a flexible coupling. The flexible coupling transmits torque between the first and second end portions. Additionally, the flexible coupling allows relative rotational displacement between the first and second end portions when the movable jaw grips an implant.

BRIEF DESCRIPTION OF THE DRAWINGS

FIG. 15 is an elevation view of the handle FIG. 4 is an elevation view of a shank for the inserter according to the second embodiment of the invention.

DETAILED DESCRIPTION

Figure 1:
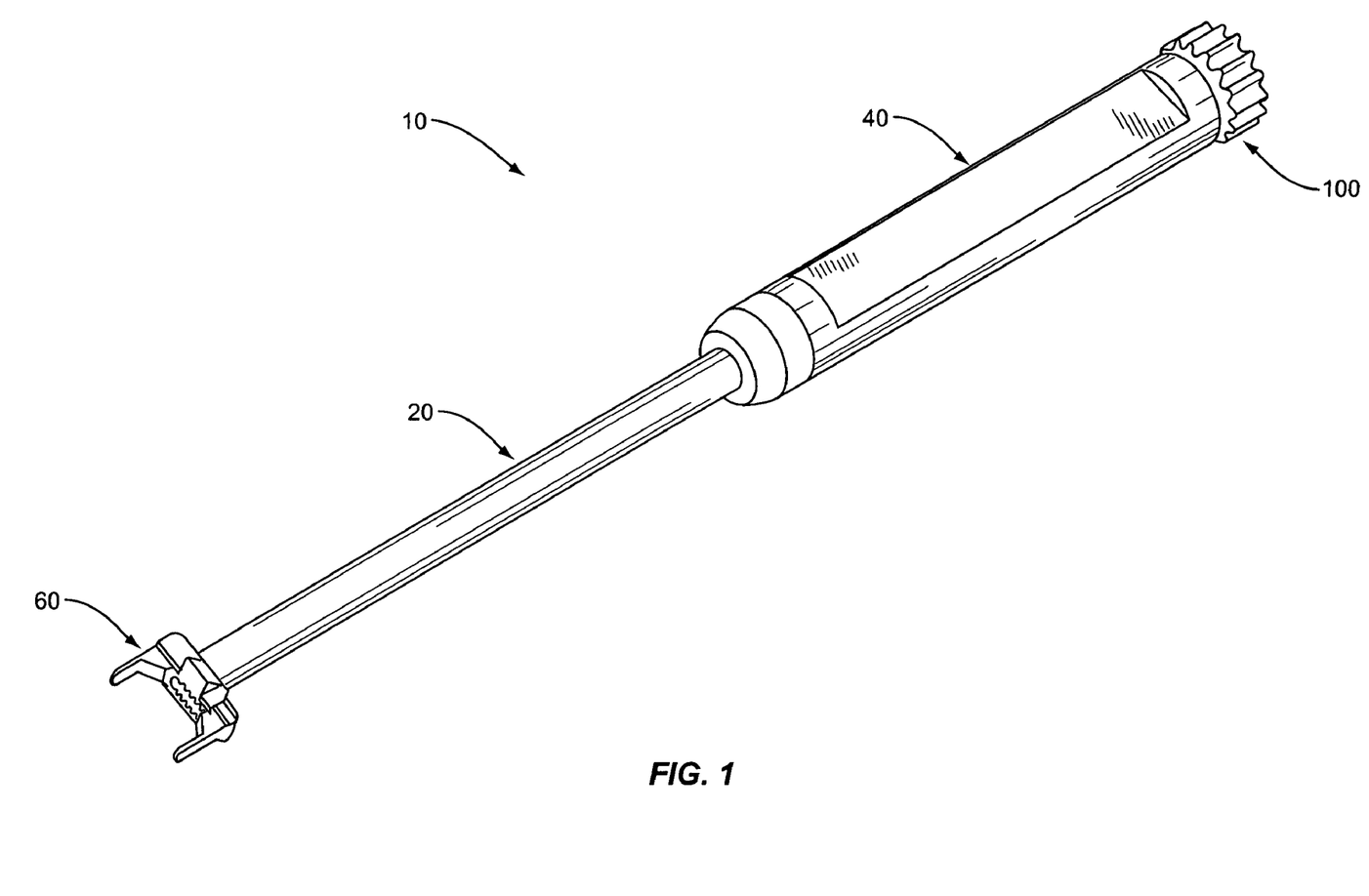
FIG. 1 is a perspective view of an inserter according to a first embodiment of the invention.
Figure 2:
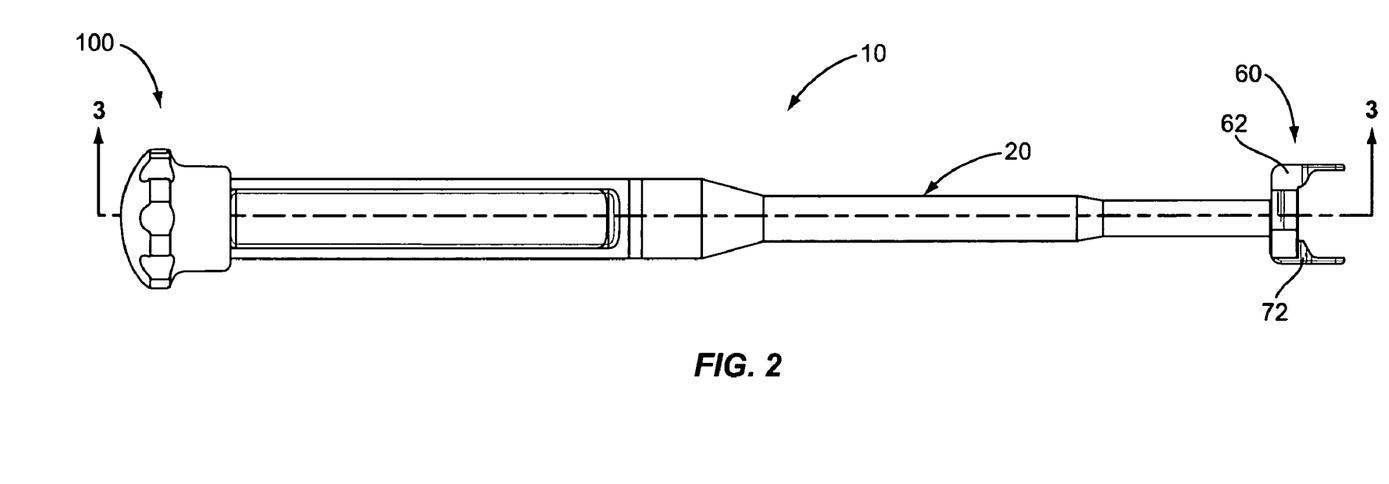
FIG. 2 is an elevation view of the inserter according to the first embodiment of the invention.
Figure 3:
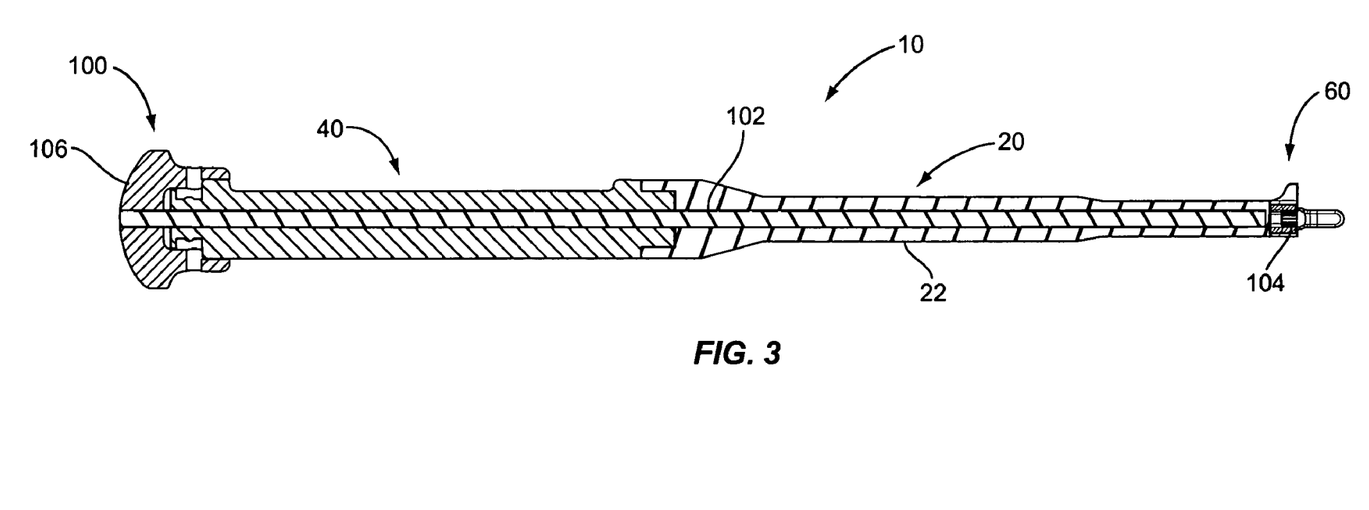
FIG. 3 is a longitudinal section view of the inserter according to the first embodiment of the invention.

Referring to FIG. 1-3, the inserter 10 of the present invention is shown therein and indicated generally by the numeral 10. The inserter 10 generally comprises a shank 20, a handle 40 at a proximal end of the shank 20, a gripping head 60 at a distal end of the shank 20, and an actuating mechanism 100 for operating the gripping head 60. The inserter 10 is designed to hold an implant while the implant is inserted into the body. The inserter 10 may be used, for example, to hold a spinal implant while the spinal implant is inserted between two vertebral members in the spine.

Figure 4:
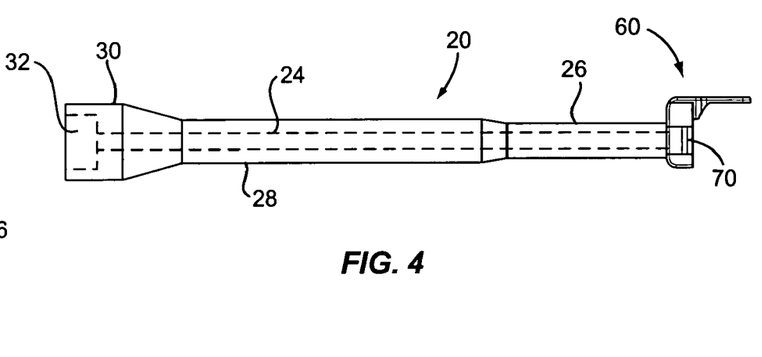
FIG. 4 is an elevation view of a shank for the inserter according to the first embodiment of the invention.

The shank 20, illustrated in FIG. 4, comprises an elongate hollow shaft 22 having an axial bore 24 formed therein. The elongate shaft 22 includes a distal end 26, an intermediate section 28, and a proximal end 30. The elongate shaft 22 increases in diameter from the distal end 26 to the proximal end 30. A cavity 32 is formed in the proximal end 30 of the elongate shaft 22 for coupling the shaft 22 to the handle 40.

Figure 5:
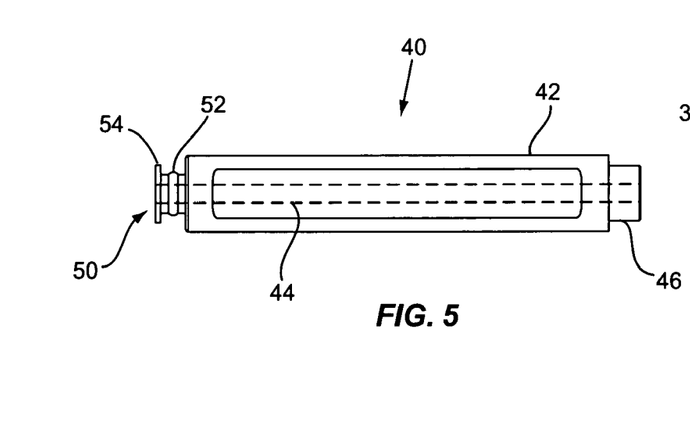
FIG. 5 is an elevation view of the handle for the inserter according to the first embodiment of the invention.

The handle 40, shown in FIG. 5, comprises a generally cylindrical main body 42 with an axial bore 44 formed therein. The handle 40 includes a first coupling member 46 on the distal end adapted to engage within the cavity 32 on the shank 20. Coupling member 46 is a cylindrical element that provides a friction fit or interference fit with the cavity 32 on the shank 20. The proximal end of the handle 40 includes a second coupling member 50. The coupling member 50 is a generally cylindrical member having a flange 54 on the outer end thereof and a raised detent ring 52 approximately midway along the length of the coupling member 50. The functions of the detent ring 52 and flange 54 will be described below.

Figures 6, 7:
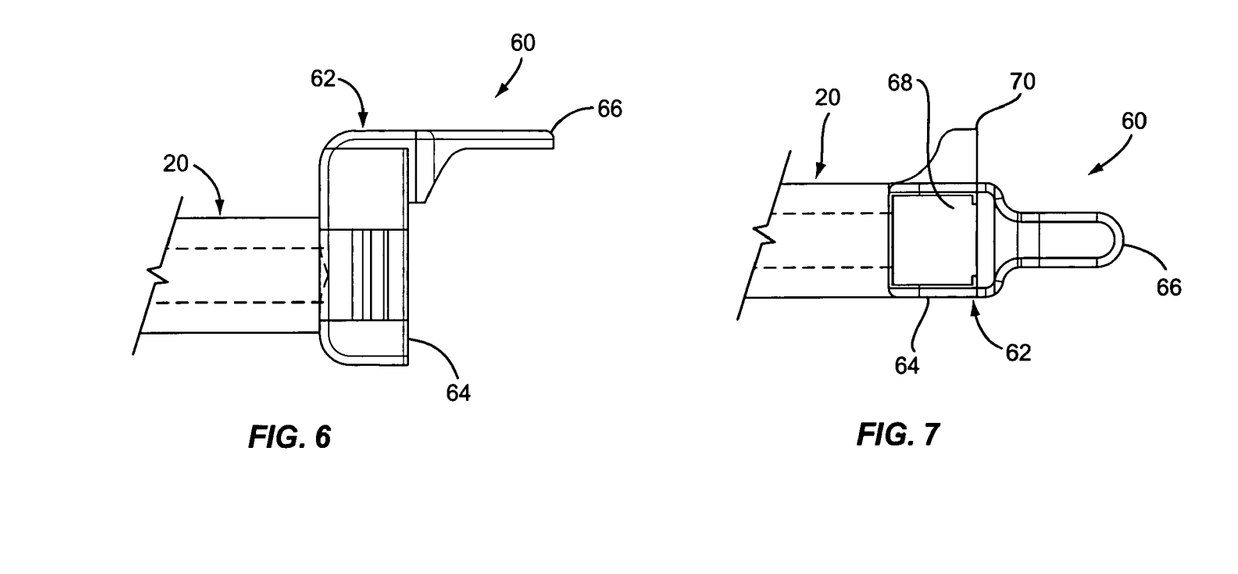
FIG. 6 is an elevation view of a gripping head for the inserter according to the first embodiment of the invention.
FIG. 7 is a top view of the gripping head FIG. 4 for the inserter according to the first embodiment of the invention.

The gripping head 60 is mounted on the distal end 26 of the shank 20. The gripping head 60 comprises a fixed jaw 62, shown in FIGS. 6 and 7, and a movable jaw 72, shown in FIGS. 8-10. The fixed jaw 62 is integrally formed with or permanently fixed to the shank 20. The fixed jaw 62 includes a base 64 and a gripping finger 66. The base 64 of the fixed jaw 62 includes a channel 68 that receives the movable jaw 72. The fixed jaw 62 may further include a stop member 70 adapted to abut against a vertebral member during an insertion procedure to aid in positioning the implant.

Figure 8:
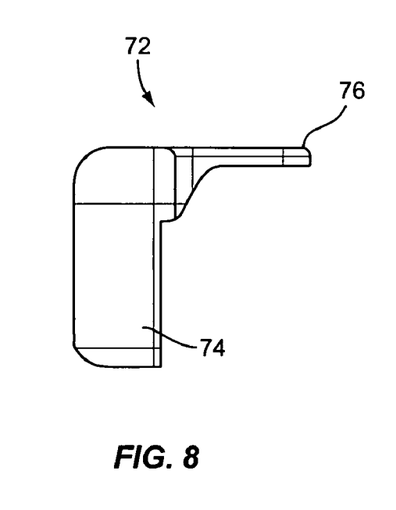
FIG. 8 is a side elevation view of a movable jaw for the inserter according to the first embodiment of the invention.
Figure 9:
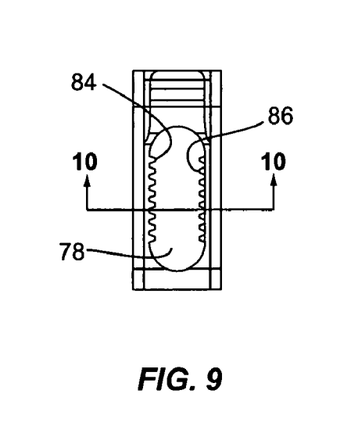
FIG. 9 is an end view of the movable jaw for the inserter according to the first embodiment of the invention.
Figure 10:
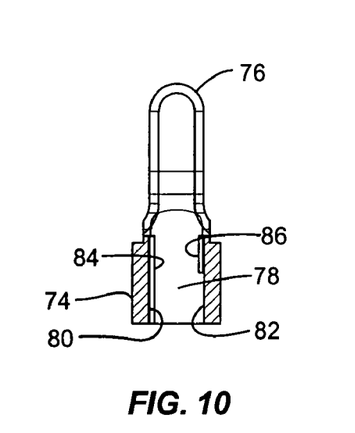
FIG. 10 is a section view of the movable jaw for the inserter according to the first embodiment of the invention.

The movable jaw 72, shown in FIGS. 8-10, comprises a slide member 74 and gripping finger 76. The slide member 74 is designed to slide within the channel 68 of the fixed jaw 62. As will be hereinafter described in greater detail, the actuating mechanism 100 can be manipulated to move the movable jaw 72 toward and/or away from the fixed jaw 62. The movable jaw 72 further includes an elongated oval-shaped cavity 78 with sidewalls 80, 82. Sidewall 80 includes a first set of teeth 84, while sidewall 82 includes a second set of teeth 86. The first and second sets of teeth 84, 86 extend in a direction generally parallel to the longitudinal axis of the inserter 10. Teeth 84 are engaged by the actuating mechanism 100 to drive the movable jaw 72. Teeth 86 function as a locking element as described more fully below.

Figure 11A:
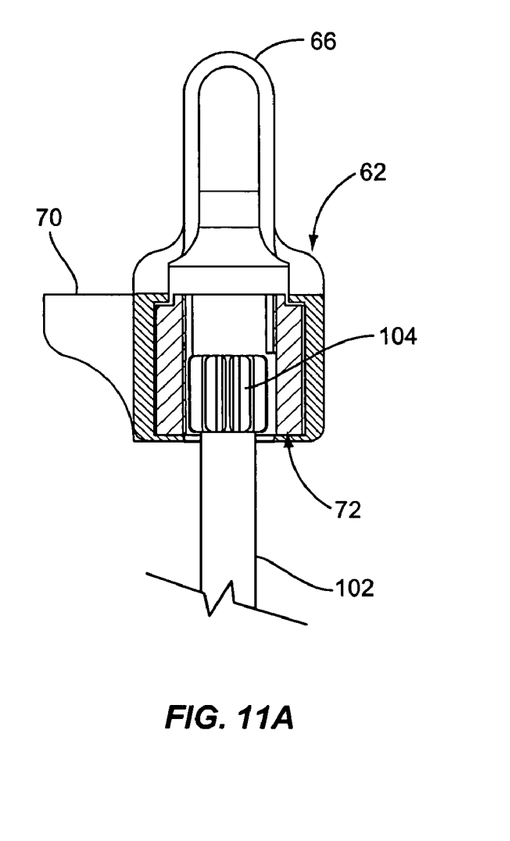
FIGS. 11A and 11B are section views of the gripping head for the inserter according to the first embodiment of the invention.
Figure 11B:
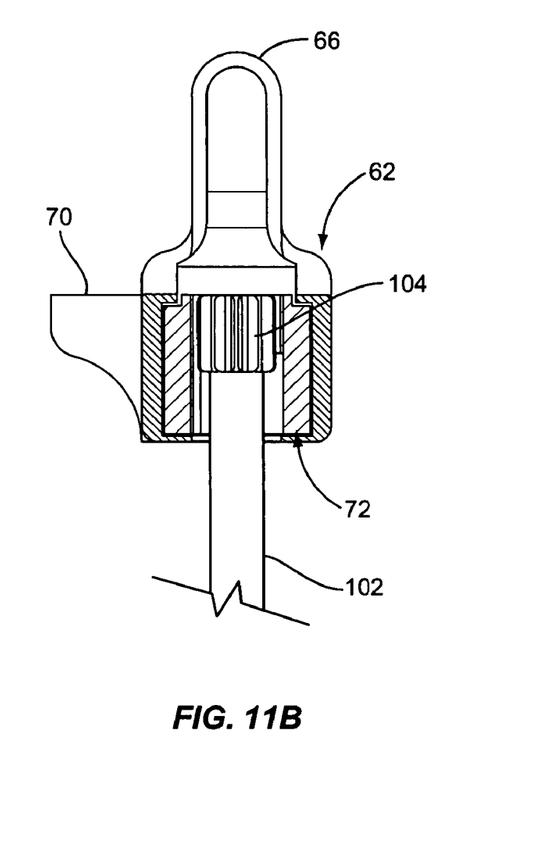

The actuating mechanism 100 comprises a drive shaft 102 with a drive gear 104 at the distal end 26 thereof. Drive gear 104 meshes with the teeth 84, 86 on the movable jaw 72. The drive shaft 102 is axially movable between a first unlocked position in which the drive gear 104 engages the first set of teeth 84 (FIG. 11A), and a second locked position in which the drive gear 104 engages both the first and second sets of teeth 84, 86 (FIG. 11B).

Figure 12A:
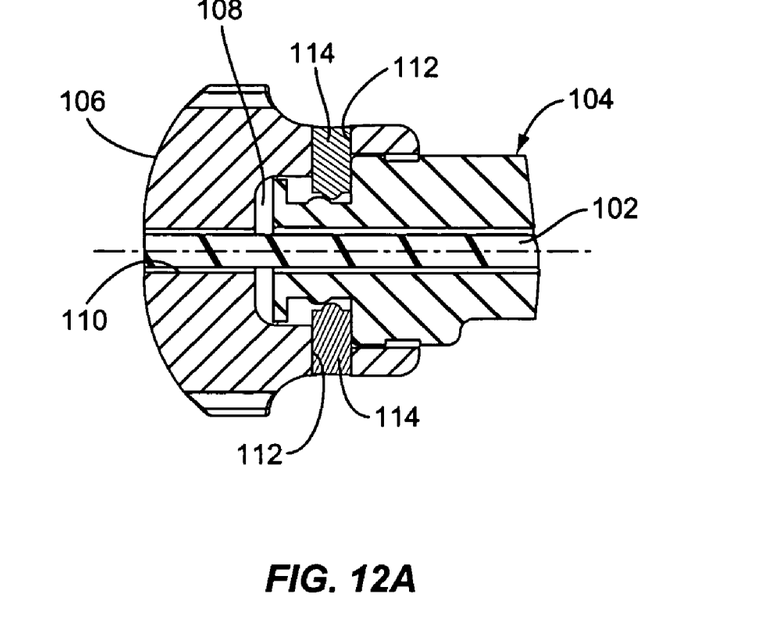
FIGS. 12A and 12B are section views showing a control knob for the inserter according to the first embodiment of the invention.
Figure 12B:
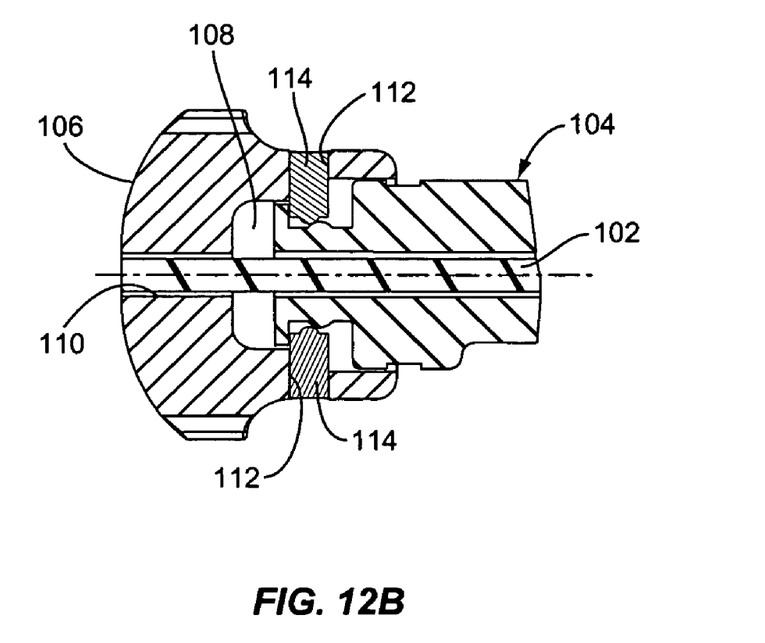

A control knob 106, shown in FIGS. 12A and 12B, is secured to the proximal end 30 of the drive shaft 102. The control knob 106 includes a cavity 108 that receives the coupling member 50 on the handle 40. The proximal end 30 of the drive shaft 102 frictionally fits into an axial opening 110 in the control knob 106. The control knob 106 includes radial openings 112 that receive set screws 114. The set screws 114 include rounded tips adapted to engage the detent ring 52 of the coupling member 50.

The control knob 106 is rotatable about the longitudinal axis of the inserter 10, and is also axially movable between a locked position (FIG. 12A) and an unlocked position (FIG. 12B). When moving between the locked and unlocked positions, the rounded tips of the set screws 114 ride over the detent ring 52. The screws 114 are tightened sufficiently so that deliberate force is required to move the control knob 106 between the locked and unlocked positions.

Figure 13:
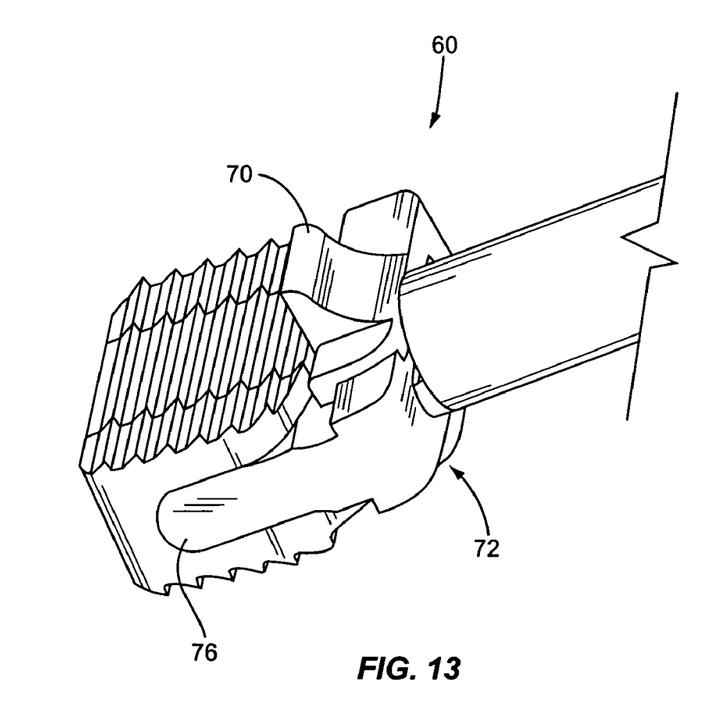
FIG. 13 is a perspective view of the gripping head holding an implant according to the first embodiment of the invention.
Figure 14:
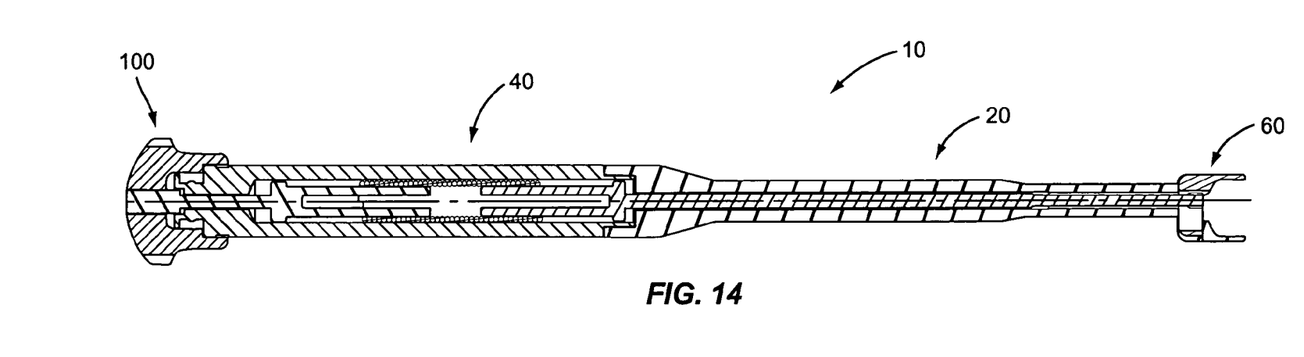
FIG. 14 is a longitudinal section view of an inserter according to a second embodiment of the invention.

When the control knob 106 is in the unlocked position (FIG. 12B), the drive gear 104 on the drive shaft 102 meshes with the first set of teeth 84 on the movable jaw 72 (FIG. 11B) such that rotation of the control knob 106 is translated into linear motion of the movable jaw 72. When the control knob 106 is turned in the first direction, the movable jaw 72 moves toward the fixed jaw 62 to grip an implant as seen in FIG. 13. When the control knob 106 is turned in a second direction, the movable jaw 72 moves away from the fixed jaw 62 to release the implant.

When an implant is firmly gripped between the fixed jaw 62 and movable jaw 72, the control knob 106 can be moved from the unlocked position (FIG. 12B) to the locked position (FIG. 12A) by applying an axially-directed force to the control knob 106. When the control knob 106 is in the locked position, the drive gear 104 on the drive shaft 102 meshes with both the first and second sets of teeth 84, 86 (FIG. 11A). Meshing the drive gear 104 with the first and second sets of teeth 84, 86 binds the drive gear 104 to prevent rotation of the drive gear 104 in either direction. Thus, the movable jaw 72 is locked in a position firmly gripping the spinal implant. To release the implant, the control knob 106 is pulled back to the unlocked position to disengage the drive gear 104 from the second set of teeth 86, thereby allowing rotation of the control knob 106. The movable jaw 72 can then be moved away from the fixed jaw to release the implant.

FIG. 14-25 illustrate a second embodiment of the inserter 10. The second embodiment of the inserter 10 is similar to the first embodiment so the same reference numbers are used in the description of the first and second embodiments to indicate similar parts. The second embodiment of the inserter 10, like the first embodiment, generally comprises a shank 20, a handle 40, and a proximal end of the shank 20, a gripping head 60 at a distal end of the shank 20, and an actuating mechanism 100 for operating the gripping head 60. The shank 20 and gripping head 60 are essentially the same in the first and second embodiments, except that the second set of teeth 86 on the movable jaw 72 is eliminated in the second embodiment. The second embodiment of the inserter 10 provides an alternate locking mechanism to prevent rotation of the drive shaft 102. More particularly, the handle 40 and actuating mechanism 100 are modified slightly to provide a mechanical interlock when the drive shaft 102 is in a locked position.

Figure 15:
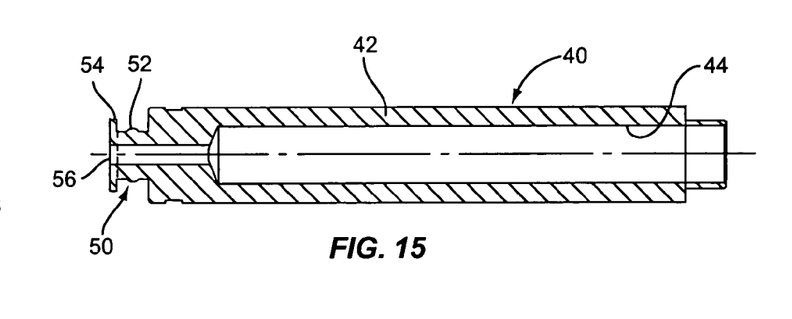
Figure 16:
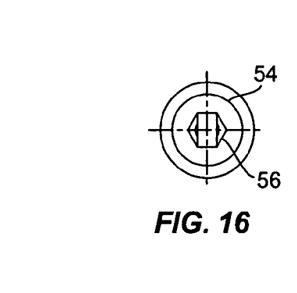
FIG. 16 is an end view of the handle for the inserter according to the second embodiment of the invention.
Figure 17:
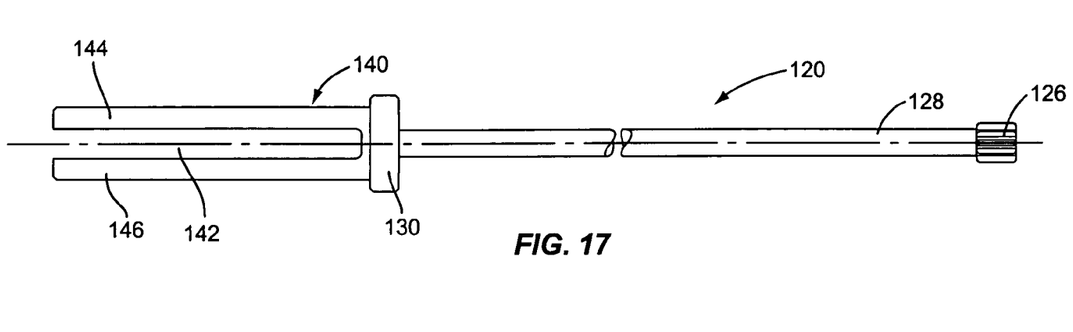
FIG. 17 is an elevation view of a first end portion of a drive shaft for the inserter according to the second embodiment of the invention.
Figure 18:
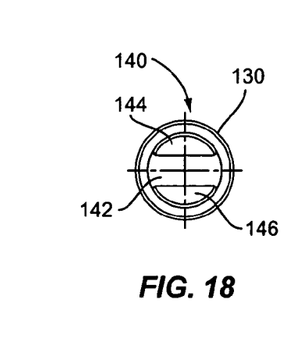
FIG. 18 is an end view of the first end portion of the drive shaft for the inserter according to the second embodiment of the invention.
Figure 19:
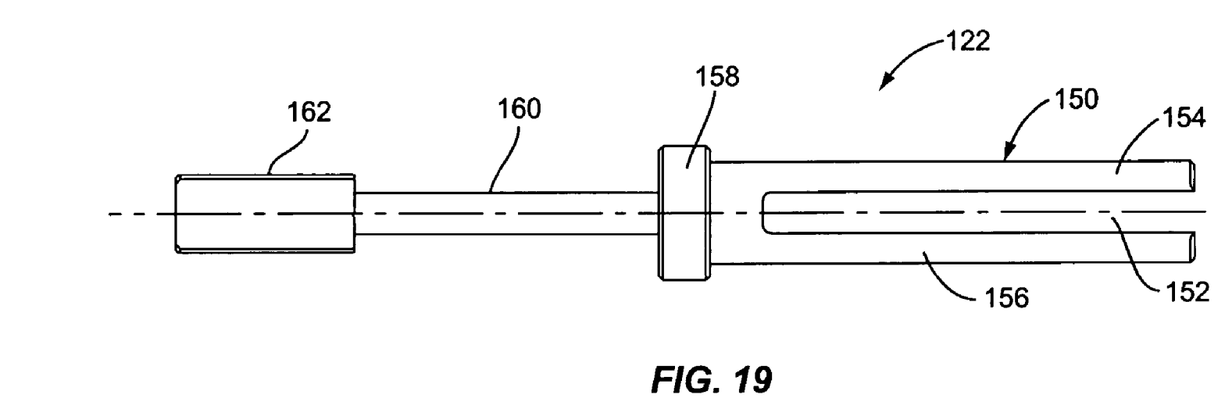
FIG. 19 is an elevation view of a second end portion of a drive shaft for the inserter according to the second embodiment of the invention.
Figures 20, 21:
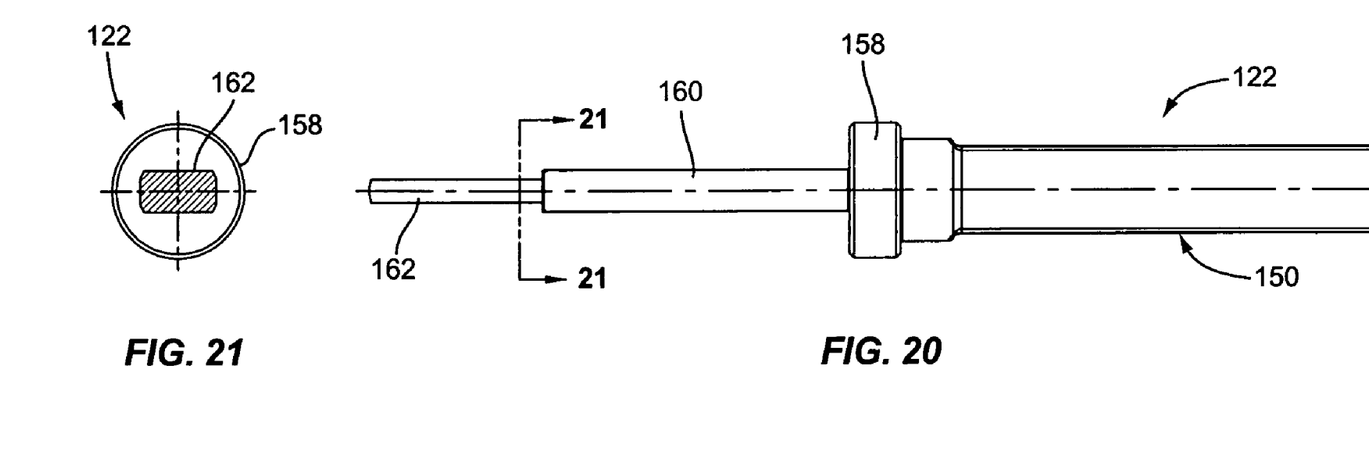
FIG. 20 is an elevation view of the second end portion of the drive shaft for the inserter according to the second embodiment of the invention.
FIG. 21 is an end view of the second end portion of the drive shaft for the inserter according to the second embodiment of the invention.

Referring to FIGS. 15 and 16, the handle 40 in the second embodiment comprises a generally cylindrical main body 42 with axial bore 44. The handle 40 includes a first coupling member 46 on the distal end adapted to engage within the cavity 32 of the shank 20. The proximal end of the handle 40 includes a second coupling member 50 having a flange 54 on the outer end thereof and a raised detent ring 52 approximately midway along the length of the coupling member 50. To the extent so far described, the handle 40 of the second embodiment is the same as the first embodiment. Additionally, the handle 40 in the second embodiment includes a hexagonal opening 56 in the coupling member 50, which forms one part of an interlock mechanism. The axial bore 44 also includes an enlarged section to accommodate a modified drive shaft 102.

Figure 22:
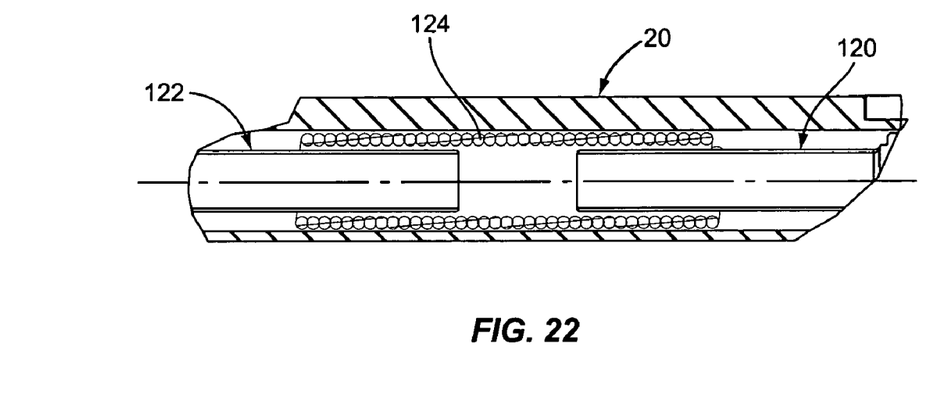
FIG. 22 is a section view of a flexible coupling for the drive shaft for the inserter according to the second embodiment of the invention.

FIGS. 17-22 illustrate the drive shaft 102 for the second embodiment. The drive shaft 102 includes a first end section 120 (FIGS. 17-18), a second end section 122 (FIGS. 19-21), and a flexible coupling 124 (FIG. 22). The first end section 120 includes a drive gear 126 disposed at the distal end of a shaft 128. Shaft 128 extends proximally from the drive gear 126 to a connecting section 130. A split shaft 140 extends proximally from the connecting section 130. The split shaft 140 includes an elongated slot 142 dividing the split shaft 140 into two fingers 144, 146. The entire end section 120 may be integrally formed, for example, by milling a steel rod.

The second end section 122 includes a split shaft 150 similar to the split shaft 140 on the first end section 120. Split shaft 150 includes an axially-extending slot 152 forming fingers 154, 156. The split shaft 150 is joined by a connecting section 158 to a single shaft 160. Shaft 160 extends approximately from the connecting section 158 to a locking element 162. The locking element 162 has a generally rectangular cross section (FIG. 21) and forms a second part of the interlock mechanism.

The first end section 120 and second end section 122 are coupled by a flexible coupling member 124 as shown in FIG. 22. The flexible coupling member 124 may, for example, comprise an extension coil spring. The ends of the extension coil spring fit tightly on the split shafts 140, 150 so that the extension spring transmits torque between the first and second end sections 120, 122 of the drive shaft 102. Additionally, the flexible coupling 124 allows some rotational displacement between the first and second end sections 120, 122 of the drive shaft 102. When axial force is applied to the drive shaft 102, the flexible coupling 124 acts as a rigid member to transmit the axial force between the first and second end sections 120, 122.

Figure 23:
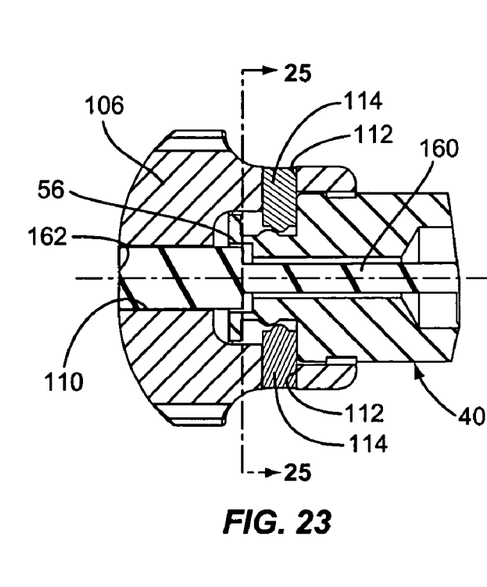
FIG. 23 is a longitudinal section view showing a control knob for the inserter in a first position according to the second embodiment of the invention.
Figure 24:
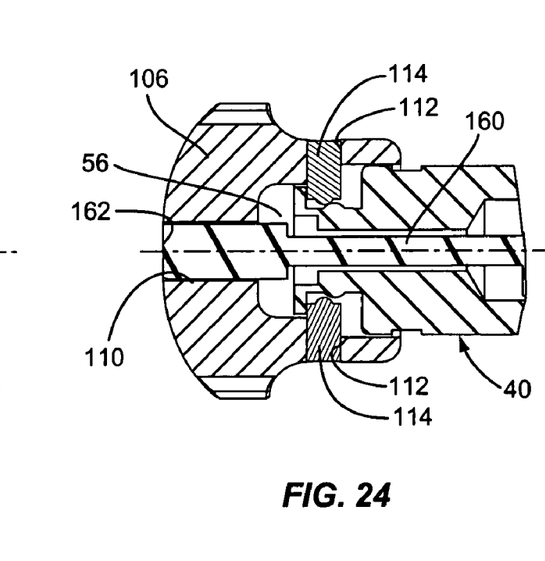
FIG. 24 is a longitudinal section view showing a control knob for the inserter in a second position according to the second embodiment of the invention.
Figure 25:
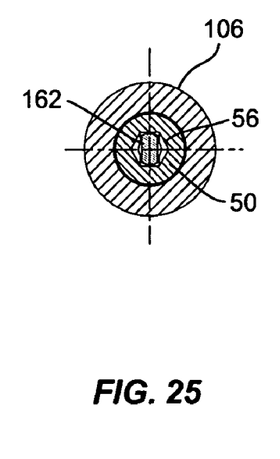
FIG. 25 is a cross-section of the control knob according to the second embodiment of the invention showing the engagement of the locking element.

Referring to FIGS. 23 and 24, the locking element 162 is received in the axial opening 110 of the control knob 106. The locking element 162 should be sized to fit tightly within the axial opening 110 so that rotation of the control knob 106 rotates the drive shaft 102. The control knob 106 is rotatable about the longitudinal axis of the drive shaft 102. Rotation of the control knob 106 causes the drive shaft 102 to rotate. Additionally, the control knob 106 is movable between a locked position (FIG. 23) and an unlocked position (FIG. 24). Set screws 114 engage the detent ring 52 on the coupling 50 so that deliberate force is required to move the control knob 106 between the locked and unlocked positions. In the locked position, the proximal end of the locking element 162 is received in the hexagonal opening 56 in the coupling member 50 of the handle 40. The engagement of the locking element 162 with the hexagonal opening 56 prevents rotation of the drive shaft 102. When the control knob 106 is moved to the unlocked position (FIG. 24), the locking element 162 disengages from the hexagonal opening 56, allowing rotation of the control knob 106 and drive shaft 102.

In operation, an implant is inserted between the fixed jaw 62 and movable jaw 72. The control knob 106 is moved to an unlocked position and rotated to close the gripping head 60 on the implant. When the implant is firmly engaged between the fixed jaw 62 and movable jaw 72, the flexible coupling 124 of the drive shaft 102 allows relative rotational displacement between the first end section 120 and second end section 122 of the drive shaft 102 to align the locking element 162 with the hexagonal opening 56. Once the locking element 162 is aligned with the hexagonal opening 56, the control knob 106 can be pushed forward to the locked position. To release the implant, the control knob 106 is pulled back to the unlocked position and rotated in a second direction to open the gripping head 60.

The invention claimed is:

1. A device for inserting an implant into a body comprising:
   a shank;
   a gripping head at one end of the shank for gripping the implant, the gripping head including a movable jaw and a fixed jaw to engage and hold the implant;
   an actuating mechanism operatively connected to move the movable jaw, the actuating mechanism including a rotatable member that is axially movable between locked and unlocked positions;
   wherein in the unlocked position, rotation of the rotatable member causes the movable jaw to move;
   wherein in the locked position, rotation of the rotatable member is prevented to lock the movable jaw in place;
   wherein the rotatable member comprises a drive shaft operatively connected with the movable jaw such that rotation of the drive shaft about a longitudinal axis causes the movable jaw to move; and
   wherein the actuating mechanism further comprises a rotatable control knob disposed at one end of a handle and connected to the drive shaft such that rotation of the control knob rotates the drive shaft.

2. The device of claim 1 wherein the drive shaft includes a drive gear at one end that meshes with a first set of teeth on the movable jaw when the drive shaft is in the unlocked position such that rotation of the drive shaft linearly translates the movable jaw.

3. The device of claim 2 wherein the movable jaw further includes a locking element to engage the drive shaft and prevent rotation of the drive shaft when the drive shaft is moved to the locked position.

4. The device of claim 3 wherein the locking element comprises a second set of teeth on the movable jaw that meshes with and binds the drive gear.

5. The device of claim 1 further including a locking element on the drive shaft that is engaged when the drive shaft is in the locked position to prevent rotation of the drive shaft.

6. The device of claim 5 further comprising a locking collar disposed around the drive shaft to engage the locking element on the drive shaft when the drive shaft is in the locked position.

7. The device of claim 6 wherein the locking collar has an opening to receive the locking element and shaped to prevent rotation of the drive shaft when the locking element is engaged within the opening of the locking collar.

8. The device of claim 1 further comprising means for locking the drive shaft against rotation when the drive shaft is in the locked position.

9. The device of claim 1 wherein the drive shaft comprises a flexible drive shaft.

10. The device of claim 9 wherein the flexible drive shaft includes first and second end sections connected by a flexible coupling that transmits torque between the first and second end sections and allows rotational displacement between the first and second end sections when the movable jaw grips the implant.

11. The device of claim 1 wherein the gripping head includes a stop member to engage a body member during insertion of the implant.

12. A device for inserting an implant into a body comprising:
    a shank;
    a gripping head at a distal end of the shank for gripping the implant, the gripping head including a movable jaw to engage and hold the implant;
    a drive mechanism including a flexible drive shaft rotatable about a longitudinal axis and having a drive gear at one end operatively connected with the movable jaw such that rotation of the drive shaft about the longitudinal axis causes the movable jaw to move; and
    wherein the actuating mechanism further comprises a rotatable control knob disposed at one end of a handle and connected to the drive shaft such that rotation of the control knob rotates the drive shaft.

13. The device of claim 12 wherein the movable jaw includes a first set of teeth that mesh with the drive gear so that rotation of the drive gear causes the movable jaw to linearly translate.

14. The device of claim 13 wherein the drive shaft is axially movable between locked and unlocked positions.

15. The device of claim 14 further comprising a locking element to engage the drive shaft and prevent rotation of the drive shaft when the drive shaft is in the locked position.

16. The device of claim 15 wherein the locking element comprises a second set of teeth on the movable jaw that meshes with and binds the drive gear.

17. The device of claim 14 further including a locking element on the drive shaft that is engaged when the drive shaft is in the locked position to prevent rotation of the drive shaft.

18. The device of claim 17 further comprising a locking collar disposed around the drive shaft to engage the locking element on the drive shaft when the drive shaft is in the locked position.

19. The device of claim 18 wherein the locking collar has an opening to receive the locking element and shaped to prevent rotation of the drive shaft when the locking element is engaged within the opening of the locking collar.

20. The device of claim 13 wherein the gripping head includes a fixed jaw.

21. The device of claim 20 wherein the gripping head includes a stop member to engage a body member during insertion of the implant.

22. The device of claim 12 further comprising means for locking the drive shaft against rotation.

23. The device of claim 12 wherein the flexible drive shaft includes first and second end sections connected by a flexible coupling that transmits torque between the first and second end sections and allows rotational displacement between the first and second end sections when the movable jaw grips the implant.

24. A device for inserting an implant into a body comprising:

a shank;
a gripping head at one end of the shank for gripping the implant, the gripping head including a fixed jaw and a movable jaw to engage and hold the implant;
a drive mechanism including a flexible drive shaft operatively connected with the movable jaw.

25. The device of claim 24 wherein the drive mechanism includes the drive gear operatively connecting the drive shaft with the movable jaw.

26. The device of claim 25 wherein the movable jaw includes a first set of teeth that mesh with the drive gear so that rotation of the drive gear cause the movable jaw to linearly translate.

27. The device of claim 24 wherein the drive shaft is axially movable between locked and unlocked positions.

28. The device of claim 27 further comprising a locking mechanism for locking the drive shaft to prevent rotation of the drive shaft.

29. The device of claim 28 wherein the locking mechanism comprises a locking element to engage the drive shaft.

30. The device of claim 27 wherein a locking element is disposed on the drive shaft and engages a fixed component.

31. The device of claim 30 further comprising a locking collar disposed around the drive shaft to engage the locking element on the drive shaft when the drive shaft is in the locked position.

32. The device of claim 31 wherein the locking collar has an opening to receive the locking element and shaped to prevent rotation of the drive shaft when the locking element is engaged within the opening of the locking collar.

* * * * *

UNITED STATES PATENT AND TRADEMARK OFFICE
CERTIFICATE OF CORRECTION

PATENT NO. : 7,608,080 B2 Page 1 of 1
APPLICATION NO. : 10/884362
DATED : October 27, 2009
INVENTOR(S) : Shipp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1460 days.

Signed and Sealed this

Twelfth Day of October, 2010

David J. Kappos
*Director of the United States Patent and Trademark Office*